United States Patent [19]

Miller et al.

[11] Patent Number: 5,871,944
[45] Date of Patent: Feb. 16, 1999

[54] SALMONELLAE PREFERENTIAL MEDIA

[75] Inventors: Russell G. Miller, Gambrills; Edward Mallinson, Columbia, both of Md.

[73] Assignee: The University of Maryland, College Park, Md.

[21] Appl. No.: 887,274

[22] Filed: Jul. 2, 1997

Related U.S. Application Data

[60] Provisional application No. 60/022,084, Jul. 9, 1996."
[51] Int. Cl.$^6$ ............................. G01N 33/569; C12N 1/20
[52] U.S. Cl. ........................................ 435/7.35; 435/253.6
[58] Field of Search ................................. 435/7.35, 253.6

[56] References Cited

U.S. PATENT DOCUMENTS 5,434,056  7/1995  Monget et al. ........................ 435/7.35

*Primary Examiner*—Herbert J. Lilling
*Attorney, Agent, or Firm*—Oblon, Spivak, McClelland, Maier & Neustadt, P.C.

[57] ABSTRACT

A new Salmonella preferential media uses lactose and cellobiose to suppress formation of black colonies by non-Salmonella, to permit easy inspection of the media to determine the presence or absence of Salmonella. Modified media, including high levels of peptone, beef extract, and tris buffers are required for preferential detection of *S. typhi*, all other Salmonella and Shigella.

13 Claims, 5 Drawing Sheets

SALMONELLAE PREFERENTIAL MEDIA

This application is a regular National application claiming priority from provisional application, U.S. application Ser. No. 60/022,084 filed Jul. 9, 1996.

BACKGROUND OF THE INVENTION

Field of the Invention

This invention pertains to a Salmonella-preferential or selective plating medium, to be used in conjunction with assays performed to determine the presence of Salmonella microorganisms in poultry, other livestock species, humans, and related environments. Other examples of Salmonella-preferential media exist, such as those described in U.S. Pat. No. 5,208,150, which is incorporated herein by reference. The MM medium (Miller-Mallinson medium) of the present invention is a significant and non-obvious improvement over the other selective media, for the reasons listed herein.

BACKGROUND OF THE PRIOR ART

Generally, when streaked or plated onto most differential and selective bacterial agar media, Salmonella spp. are at an immediate disadvantage compared to other bacteria. This is because there tends to be more growth factors favoring the competing bacteria than favoring the Salmonella spp. Several media use a high concentration of carbohydrates to differentiate Salmonella competitors from Salmonella on the basis of the media color changes due to decreased pH associated with the growth of such competitors as $E.\ Coli$ and Enterobacter spp. The exact change in color is dependent on the type of pH change indicator used in the media. Because Salmonella spp. usually are unable utilize most of the carbohydrates that the competing bacteria are capable of metabolizing, the other competing bacteria tend to outcompete the Salmonella on the carbohydrate-rich medium, and the presence and number of Salmonella organisms in a test sample often are masked from efficient detection.

For instance, Hektoen Enteric Agar (HEK)(multiple commercial sources- Difco, BBL, etc.) contains a total of 26 g/L of carbohydrate (12.0 g/L lactose, 12.0 g/L saccharose, and 2.0 g/L salicin). None of these carbohydrates were added to benefit the growth of Salmonella spp. On the other hand, Bismuth Sulfite Agar (BSA) multiple sources) with only one carbohydrate-glucose, appears to improve the chance that Salmonella spp will grow and be detectable on the agar. In this instance, however, the selection of glucose is not a good choice, because all of the members and many non-members of the bacterial family Enterobacteriaceae (in which Salmonella belong) utilize glucose, providing no real advantage in selecting for Salmonella spp.

$H_2S$ production is characteristic of most Salmonella spp., and the resulting black color of a bacterial colony in or on a growth medium is commonly used to advance the detection of Salmonella. Due to the ability to utilize lactose preferentially before utilizing certain proteinaceous media ingredients (with the production of $H_2S$ and a black color change in the media/colony), it is advantageous to so formulate the media that most common lactose-fermenting non-salmonellae are not driven to utilize the proteinaceous components of the media and produce black colonies. A modest percentage of Salmonella strains do ferment lactose, however, and therefor Salmonella may not be detected in media containing an extensive amount of lactose. Media with relatively low levels of glucose and higher levels of lactose are not particularly suitable for the detection of Salmonella through the detection of black colony formation.

The identification of Salmonella spp. by the detection of black colony ($H_2S$) formation is further complicated by the fact that several other non-salmonellae do produce black colonies under certain conditions (e.g., high protein media, low oxygen tension, etc.). Media of low selectively may allow excessive numbers of low or asaccharolytic bacteria, such as $H_2S$-positive Proteus ssp to thrive. XLT4 in common use in poultry laboratories, does not detect as many weak $H_2S$ producers (15%) as would be desirable.

SUMMARY OF THE INVENTION

To reduce the aforementioned shortcomings, a new approach was attempted. The objective was to create an agar medium that would encourage both the growth and the identification of Salmonella spp. Based on results of preliminary studies, a new medium was created that was composed of 1.2 g each of D-mannitol and D(+) trehalose, and 5.0 g each of alpha-lactose and D-(+)-cellobiose. The very unique choice of balanced levels of lactose and cellobiose was to suppress the formation of black colonies by non-salmonellas that could otherwise be confused with colonies of Salmonella organisms. The concentration chosen for lactose was effective for two reasons. Firstly, the lactose concentration was not enough to inhibit the production of black colonies from lactose-fermenting Salmonella. Secondly, lactose combined with the 5.0 g of cellobiose considerably reduced the numbers of false-positive, black colonies of non-salmonella organisms. The invention media (MM Media) is carefully balanced to allow detection of those salmonellae with proclivity to occasionally utilize lactose, but to reduce false-positive $H_2S$ reactions in strongly lactose-utilizing non-salmonellae. The absence of glucose as compared to its presence in BSA agar, promotes the ability of the inventive media to detect $S.\ typhi$ (a major lethal human pathogen). $S.\ typhi$ is often a weak producer of $H_2S$ and black colonies. BSA is a medium commonly used for isolation of $S.\ typhi$. Further, the total formulation, including increased levels of peptones, beef extract, and tris buffers, promotes the better detection of many common Salmonella (possibly 15%) which are poor $H_2S$/black colony producers and easily missed in the laboratory.

In addition to $H_2S$ formation, lactose fermentation is also an important feature that helps distinguish most Salmonella spp from their competitors on selective differential agar media. For this reason, 5-bromo-4-chloro-3-indolyl-beta-D-galactopyranoside (X-gal) is included in the MM medium formulation. When a galactopyranosidase-producing bacterium splits off galactose from lactose, the pigmented chromophores stimulate a bright bluish-green color change. In MM media, this phenomenon is used instead of pH to demonstrate lactose fermentation, consequently blue-green colonies with no black centers are basically ruled out as Salmonella. Eliminating accidity (low pH) for colony color differentiation fiber improves the growth of Salmonella and their ability to produce $H_2S$ and black colonies. The occasional colony with a black center and a blue-green edge would require further evaluation. Niaproff4® (sodium 7-ethyl-2-methyl-4-undecyl sulfate) (old name: Terigitol 4) is added to suppress growth of competitor bacteria.

The invention encompasses two media formulations: MM for the more common Salmonella; and, MMt, an especially peptone-beef extract-rich medium specifically designed for the more fastidious human pathogen, $S.\ typhi$.

BRIEF DESCRIPTION OF THE FIGURES

FIG. 1 is a photograph of five plates, the media in the upper two plates labeled BSA and HEKT identify available media commonly used for isolation of Salmonella while the lower row of three agar plates reflects the inventive media. All five media were streaked with a single strain of *S. typhi*.

FIG. 2 is a photograph of three commercial plates (BSA, HEKT and XLD) compared with the inventive plate identified as MM. These plates reflect overnight incubation (O/N).

FIG. 3 is a photograph of a plate of the inventive media and a reference, streaked with the same strain of a lactose fermenting non-Salmonella sp. The difference between the two MM formulae is that the one on the left contains 5.0 g of lactose per liter, while the one on the right (w/o) is without any lactose.

FIG. 4 reflects the use of an embodiment of the invention suitable for the identification of *S. typhi*. The MMt plate on the left, as indicated, contains 5.0 g of lactose, while the one on the right has 30.0 g of lactose per liter.

FIG. 5 is a photograph of an inventive plate on which *Shigella flexneri* has been cultured. As with FIGS. 3 and 4, the culturing has been done overnight (O/N).

DETAILED DESCRIPTION OF THE INVENTION

Figure 1:
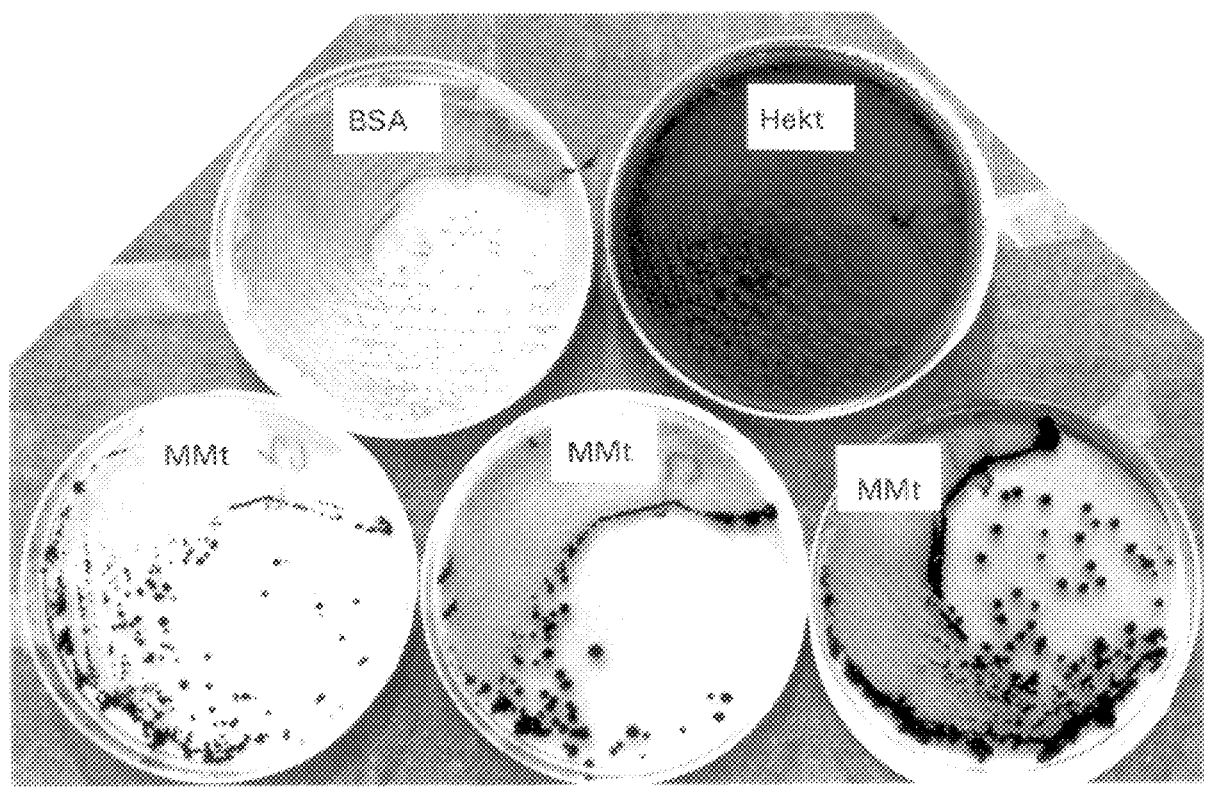
FIGS. 1–5 are xerographic reproductions of photographs of actual culture plates employing the inventive media.
Figure 2:
Figure 3:
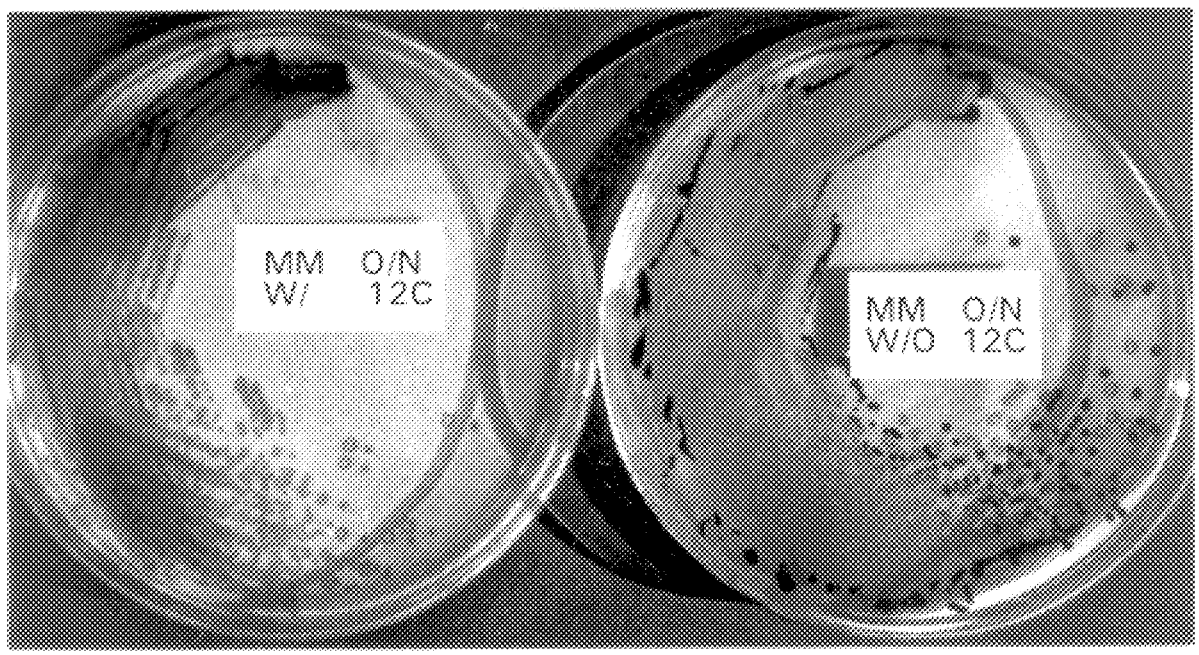
Figure 4:
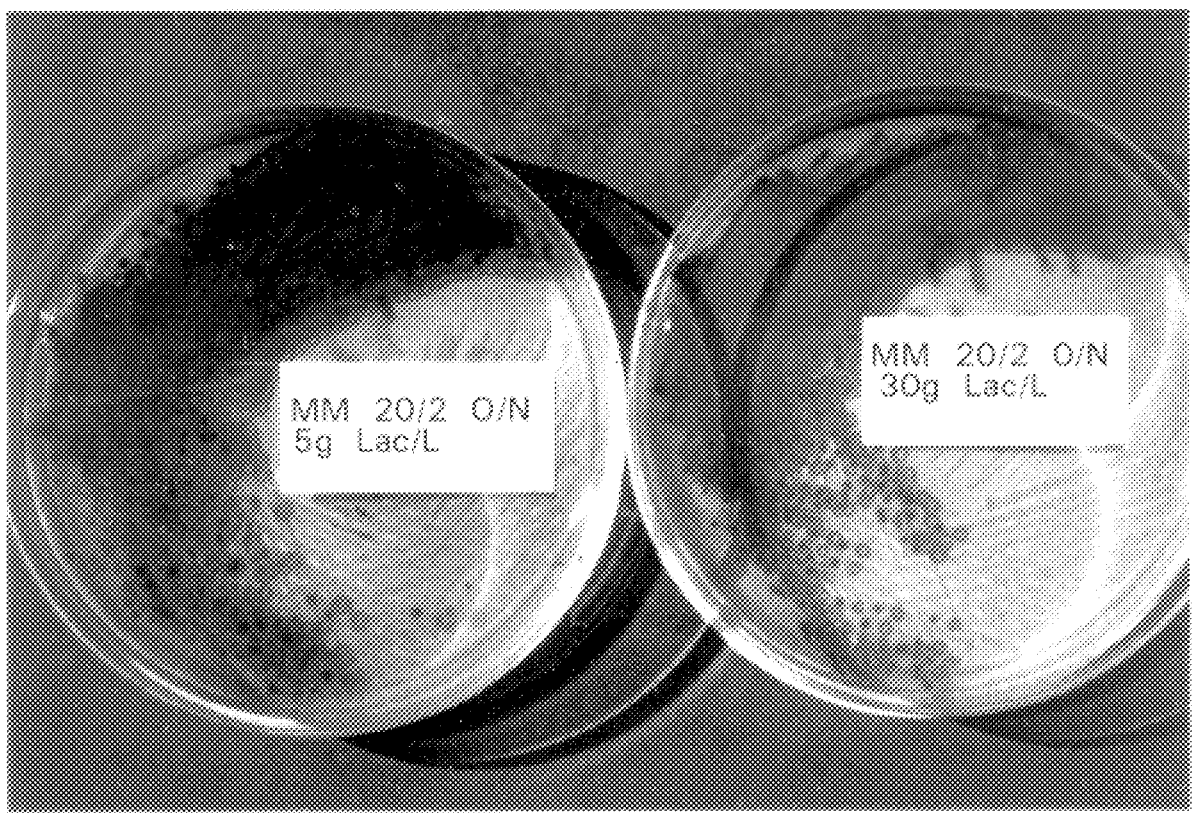

The inventive media, referred to herein as MM, and MMt are a carefully balanced media, which include as essential elements D-mannitol and D(+) trehalose both in amounts of 0.5–5.0 g/L, together with α-lactose in an amount of 4–40 g/L and D-(+)-cellobiose in an amount of 3–7 g/L and peptone in an amount of 2–26.0 g/L.

Following is an Example of an initial formulation of the MM medium:

EXAMPLE 1
(amount per liter of water distilled or demineralized water)

| Yeast Extract | 3.0 g | alpha-lactose | 5.0 g |
|---|---|---|---|
| Ferric Ammonium Citrate | 0.8 g | D-(+) cellobiose | 5.0 g |
| Sodium Thiosulfate | 6.8 g | D-Mannitol | 1.2 g |
| Trizma ® Base | 0.7 g | D(+) Trehalose*H$_2$O | 1.3 g |
| Trizmahydrochloride ® | 2.3 g | NaCl | 3.0 g |
| Purified agar | 15.0 g | Niaproof4 (Tergitol4) | 4.5 ml |
| X-gal | 0.1 g | | |
| Polypeptone peptone | 5.0 g | | |

1. Weigh or measure each of the above ingredients, and mix to 1.0 L distilled water in a 2 L or larger Erlenmeyer flask. If desired, X-gal (0.1 g) is dissolved in 1 ml. of N,N-dimethyl formamide and then added to the other ingredients. Alternatively X-gal may be added directly.

2. Bring to a boil for one minute.

3. Remove from heat source and cool in a water bath to 45°–50° C.

4. Pour plates. Finished medium should be 4–5 mm thick.

5. Allow plates to remain at room temperature overnight, before storing at 2°–5° C. in well-sealed plastic bags.

While it is preferred to use X-gal in an amount of 0.05–0.5 g/L in every embodiment of the invention, this adds expense. With rate exceptions, X-gal may be omitted from the media.

(1) The exceptions are when culturing: for:
  (a) Shigella spp—without X-gal, all lactose-fermenting colonies would have the same color appearance as shigellae. Colony color differentiation between shigellae and the lactose-fermenting bacteria would be lost. When X-gal is split by the lactose fermenters, the green pigmented colonies produced can be easily differentiated from the non-pigmented colonies of shigellae.

(b) *S. Typhi*—Because of the nutritional demands of *S. Typhi*, the isolation medium MMt was highly enriched. The concession of increased enrichments also promotes growth of competitors that similarly exhibit black colonies, which could be confused with *S. Typhi*. Fortunately these non-salmonellae are lactose fermenters, so their colonies can be distinguished by the green pigment produced, when they split X-gal. These competitors exhibit colonies with green borders and black centers. Salmonella colonies typically have non-pigmented borders and black centers.

The reason for the broad range of the constituent amounts stated in this application is due to the wide variety of samples that may be taken to detect Salmonella or Shigella. Laboratories may receive samples from sick or carrier humans, pets, food animals or farms, food processors or related environments.

In addition to Example 1, the two following formulae are recommended as the most practical with the caveat that each can be modified to a particular sampling requirement.

A. Formula One, designated MM, is applicable for the more commonly isolated sahnonellae and shigellae, (i.e., any sample that is not a suspect *S. Typhi* sample).

| MM medium (constituent sample amounts as per Liter) | |
|---|---|
| polypeptone peptone | 3.5 g |
| beef extract, desiccated | 2.0 g |
| yeast extract | 3.0 g |
| α-lactose | 5.0 g |
| D-(+)-cellobiose | 5.0 g |
| D-mannitol | 1.2 g |
| D(+) trehalose | 1.2 g |
| sodium chloride | 3.0 g |
| ferric ammonium citrate | 0.8 g |
| sodium thiosulfate | 6.8 g |
| TRIZMA ® base (Tris[hydroxymethyl] aminomethane) | 0.7 g |
| TRIZMA ® hydrochloride (Tris[hydroxymethyl] aminomethane hydrochloride) | 2.3 g |
| X-gal (5 bromo-4chloro-3-indolyl-beta-D-galactopyonoside) | 0.1 g |
| purified agar | 15.0 g |
| Niaproof 4 ® | 4.5 ml |
| distilled or demineralized water | 1000 ml |

Weigh together all the dry ingredients. Mix thoroughly in the distilled/demineralized H$_2$O to dissolve, and with pipette add the 4.5 ml of Niaproof 4. Bring to a boil one minute to melt agar. Temper in a 45.0° C. to 50.0° C. water bath, and dispense approximately 20 ml of medium per 15×100 mm sterile petri dish.

B. Formula Two, designated MMt, is enriched with additional polypeptone peptone. The medium is not only enriched to improve growth, but also to produce good black colonies that identify suspect *S. Typhi*. The "t" in MMt stands for the species name typhi in *S. Typhi*, and thereby identifies this formula as the medium of choice for the isolation of *S. Typhi*, the cause of deadly human typhoid fever. Although *S. Typhi* is rare in the U.S.A., it is common in many underdeveloped countries.

Because MMt is enriched, it would of course support the growth of the less nutritionally demanding salmonellae. Nevertheless, MMt is not recommended as a general purpose Salmonella isolation medium. It is more expensive than MM, is not needed for the isolation of the majority of salmonellae found in nature, and may produce the increased growth of competing and confusing background bacterial colonies.

Since Shigella like *S. Typhi* is a human pathogen, and is found in similar sample types, it is more likely to be found in plating/detection situations where MMt is being employed.

| MMt medium (amounts are per Liter) changes from MM medium. | |
| --- | --- |
| polypeptone peptone | 22.0 g |
| beef extract, desiccated | 4.0 g |
| α-lactose | 5.0 g or up to 30.0 g as determined by the nature of the specimen |

One of the primary features of the MM media is the relative scarcity of fermentable sugars in the growth medium. In the case of clinical samples where Salmonella are suspected, however, it may be desirable to increase the richness of the medium. This can be accomplished by adding additional peptone. The total amount of peptone may be in the range of up to approximately 2.0–26.0 g/L. Additionally, when peptone is below about 5.0 g/L, dessicated beef extract may be present in amounts of 0–6.0 g/L. When peptone levels are above about 15 g/L, it is desirable to also add urea to the medium, to inhibit growth by other types of bacteria. Salmonella are slightly inhibited by urea, so their growth will not be inhibited by low levels of urea in the medium. The amount of urea that can be added in combination with the additional peptone is in the range of 5 to 15 g/L. Lactose may be present in amounts of 4.0–40.0 g/L. In addition, phenol red dye can be added as a pH indicator, at a concentration of about 0.012 to 0.024 g/L. The addition of phenol red allows the identification of non-salmonella that break down urea and thereby create a pH increase in the surrounding medium.

Agar may be added to the medium or omitted. If agar is added to the medium, it is typically in the range of 13–20 g/L. It should be noted that Niaproof4® (N4) may be antagonistic to certain elements of available agars, the result of adding certain concentrations of N4 thereto being an increase in competing organisms.

The success of the MM medium can be seen in the experimental results listed in Tables 1 and 2. Table 1 shows the efficiency of Salmonella detection using the MM media compared to the LT4 media acquired from the indicated commercial sources. Table 2 shows the control of background coliform and pseudomonad competitors on both MM medium and XLT4 medium.

Experimental Culturing Results

The selectivity of the inventive media for Salmonella is reflected in FIGS. 1–5 hereof, which are xerographic reproductions of color photographs. The color photo originals, which demonstrate selectivity much better, are available from the inventor. In FIG. 1, the three lower plates of MM media are compared with two commercial upper plates, BSA and HEKT. All five media were streaked with a single strain of *S. typhi*. Suspect Salmonella, whether *S. typhi* or any other Salmonella sp. would be depicted by colonies with black centers. As can be seen, neither commercial media shows even a hint of colonies with black centers. (The darker coloration of HEK in FIG. 1 is due to its natural blue color). In contrast, the three inventive plates, designated MMt display very definite black centered colonies. The deadly human pathogen, *S. typhi*, would have been per liter. This level of lactose could be advantageously used with either the general or enriched formula. In particular, when monitoring for typhoid fever, the 30.0 g lactose formulation is preferred.

Figure 5:
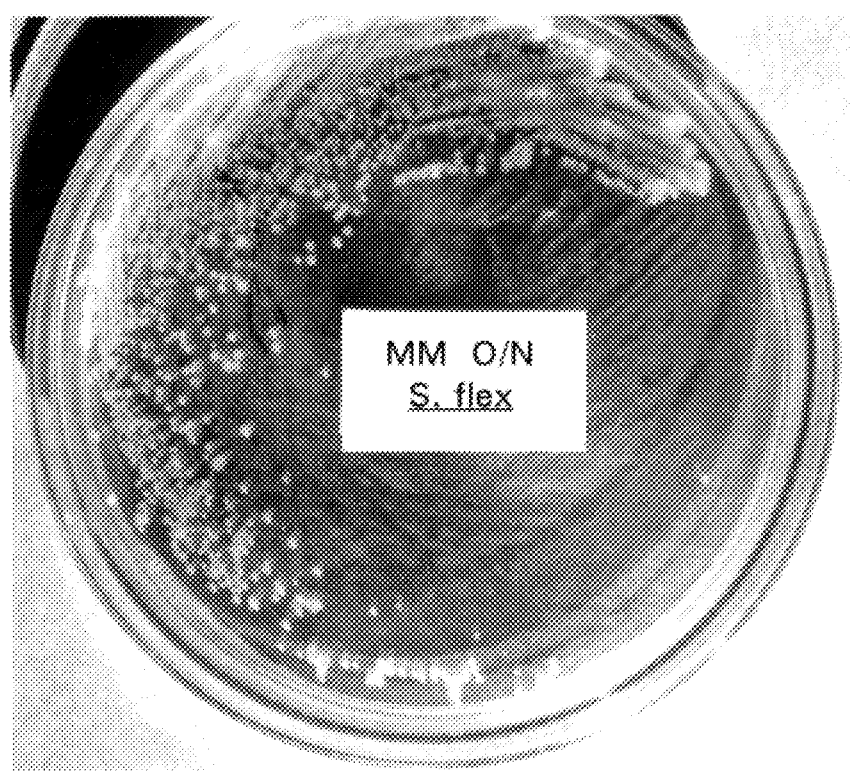

Shigella are isolated essentially from the same sources as *S. typhi*. They do not produce black colonies or green pigment, so they are readily differentiated from Salmonella and lactose fermenting bacteria. FIG. 5 reflects plain, white colonies that are an outgrowth from samples of human origin of Shigella, particularly *Shigella flexneri*.

The concentrations listed above are provided as an example of the best mode of the invention. Some variation in the concentration of components is possible without losing the benefits of the invention, and these can be routinely determined. Alternatives will occur to those skilled in the art, particularly in the selection of base agars, holding media, plating media and the like, without the exercise of inventive faculty, and without departing from the scope of the invention.

TABLE 1

Quail carcass rinse study: Salmonella detection efficiency using filter membranes transferred to either XLT4 or MM agar and pads.

| Post-transfer[C] media and incubation format | Number Salmonella colonies detected for 4 ml of carcass rinse by morphology[A] or by colony lift immunoassay[B] | | | | | |
| --- | --- | --- | --- | --- | --- | --- |
| | Replicate No. 1 | | Replicate No. 2 | | Replicate No. 3 | |
| | Morphology | Immunoassay | Morphology | Immunoassay | Morphology | Immunoassay |
| 8 hours/35 C. | | | | | | |
| XLT4 agar[D] | 2 trace | Not Done(ND) | 5 trace | 8 | 5 trace | ND |
| MM agar[E] | 5 obvious | Not Available (NA) | 4 obvious | ND | 6 obvious | ND |
| XLT4 pad[F] | 0 | NA | 0 | 5 | 1 obvious | ND |
| MM pad[G] | 10 obvious | NA | 4 obvious | 6 | 3 obvious | ND |
| 27 hours/35 C. | | | | | | |
| XLT4 agar[D] | 2 obvious 1 trace | NA | ND | ND | 6 obvious 5 trace | 11 |
| MM agar[E] | 5 obvious | NA | ND | ND | 6 obvious | 6 |

TABLE 1-continued

Quail carcass rinse study: Salmonella detection efficiency using filter membranes transferred to either XLT4 or MM agar and pads.

| Post-transfer[C] media and incubation format | Number Salmonella colonies detected for 4 ml of carcass rinse by morphology[A] or by colony lift immunoassay[B] | | | | | |
|---|---|---|---|---|---|---|
| | Replicate No. 1 | | Replicate No. 2 | | Replicate No. 3 | |
| | Morphology | Immunoassay | Morphology | Immunoassay | Morphology | Immunoassay |
| XLT4 pad[F] | 8 obvious 2 trace | 12 | ND | ND | 2 obvious 3 trace | 8 |
| MM pad[G] | 11 obvious | 11 | ND | ND | 2 obvious 2 trace | NA |

[A]Obvious colonies were totally jet black, trace colonies were tan with greyish center.
[B]Used KPL system (common structural antibody).
[C]Pretransfer novobiocin-membrane tetrahionate resuscitation treatment was for 18 hours at 35 C.
[D]Standard XLT4 agar preparation (Difco).
[E]New Miller-Mailinson (MM) agar.
[F]BPW-rehydrated XLT4 pad from FMT.
[G]Agarless MM formulation on filter pad supplied by FMT.

TABLE 2

Quail carcass rinse study: Control of background coliform and pseudomonad competitors with filter membranes transferred to either XLT4 or MM agar and pads.

| Post-transfer[A] 26-hour 35 C. incubation of filter membranes on LXT4 or MM agar and pads | Visual counts of coliforms and pseudomonads[a] | | | | | | | | |
|---|---|---|---|---|---|---|---|---|---|
| | Replicate No. 1 | | | Replicate No. 3 | | | Total replicate Sets No. 1 and 3 | | |
| | Coliforms | Pseudomonads | Total | Coliforms | Pseudomonads | Total | Coliforms | Pseudomonads | Total |
| XLT4 agar | 17 | 13 | 30 | 20 | 30 | 50 | 31 | 43 | 80 |
| MM apr | 24 | 35 | 59 | 28 | 50 | 78 | 52 | 85 | 137 |
| XLT4 pad | 12 | 12 | 24 | 45 | 20 | 65 | 57 | 32 | 89 |
| MM pad | 12 | 19 | 31 | 7 | 32 | 39 | 19 | 51 | 70 |

[A]Prior to transfer of filter membranes to agar or pads, the membranes were treated with novobiocin (5 mcg/ml) m-totrathionate broth for 16 hours at 35 C.
[a]Counts for replicate set no. 2 were unavailable after 27 hours of incubation. Replicate set no. 2 was sent to another laboratory (KPL) for colony lift immunoassays.

What is claimed is:

1. A Salmonella preferential media, comprising peptone in an amount of 2–26.0 g/L, D-mannitol in an amount of 0.5–5.0 g/L, D(+) trehalose in an amount of 0.5–5.0 g/L, lactose in an amount of 4–40 g/L and D(+) cellobiose in an amount of 3–7 g/L, wherein said media further comprises water.

2. The media of claim 1, further comprising 5-bromo-4-chloro-3-indolyl-β-D-galactopyranoside (X-gal) in an amount of 0.05–0.5 g/L.

3. The media of claim 1, wherein said media further comprises agar in an amount of 13–20 g/L.

4. The media of claim 1, wherein the peptone in said media is below about 5.0 g/L, and said media further comprises dessicated beef extract in an amount of 0–6.0 g/L.

5. The media of claim 1, wherein said peptone is present in an amount above about 15 g/L, and said media further comprises urea in an amount of 5–15 g/L.

6. The media of claim 1, wherein said media further comprises phenol red dye in an amount of 0.012–0.024 g/L.

7. The media of claim 1, wherein said media supports the growth of S. typhi, and comprises peptone in at least 22.0 g/L.

8. The media of claim 7, wherein said media further comprises dessicated beef extract in an amount of 4.0 g/L.

9. The media of claim 1, wherein said media further comprises sodium 7-ethyl-2-methyl-4-undecyl sulfate.

10. The media of claim 1, further comprising Tris [hydroxymethyl]aminomethane, in an amount of 0.5–1.0 g/L.

11. The media of claim 1, further comprising Tris [hydroxymethyl]aminomethane hydrochloride in an amount of 2.0–2.5 g/L.

12. A method of selectively growing Salmonella suspected of being present in a sample, comprising streaking the medium of claim 1 with a representative portion of said sample, and incubating said streaked media under conditions conducive to the growth of Salmonella, and inspecting said media after said incubation for Salmonella colonies.

13. The method of claim 9, wherein said sample is suspected of harboring S. typhi, and said media comprises at least 22.0 g/L peptone and 5.0–30.0 g/L lactose.

* * * * *